United States Patent
Park et al.

(10) Patent No.: US 12,343,183 B2
(45) Date of Patent: Jul. 1, 2025

(54) DENTAL SUPPORT BLOCK, AND IMAGING DEVICE COMPRISING SAME

(71) Applicant: THE SLEEP FACTORY INC., Incheon (KR)

(72) Inventors: Young Hyon Park, Incheon (KR); Hyun Jin Choi, Incheon (KR); Jun Young Park, Incheon (KR); Jun Won Park, Incheon (KR)

(73) Assignee: THE SLEEP FACTORY INC., Incheon (KR)

( * ) Notice: Subject to any disclaimer, the term of this patent is extended or adjusted under 35 U.S.C. 154(b) by 1129 days.

(21) Appl. No.: 16/645,402

(22) PCT Filed: Sep. 3, 2018

(86) PCT No.: PCT/KR2018/010207
§ 371 (c)(1),
(2) Date: Jun. 29, 2020

(87) PCT Pub. No.: WO2019/050231
PCT Pub. Date: Mar. 14, 2019

(65) Prior Publication Data
US 2023/0181129 A1  Jun. 15, 2023

(30) Foreign Application Priority Data

Sep. 7, 2017 (KR) .......................... 10-2017-0114362

(51) Int. Cl.
*A61B 6/04* (2006.01)
*A61B 6/00* (2006.01)
*A61B 6/51* (2024.01)

(52) U.S. Cl.
CPC .......... *A61B 6/0407* (2013.01); *A61B 6/4441* (2013.01); *A61B 6/51* (2024.01)

(58) Field of Classification Search
CPC ....... A61B 6/0407; A61B 6/14; A61B 6/4441; A61B 6/501; A61C 19/04; A61C 19/045
See application file for complete search history.

(56) References Cited

U.S. PATENT DOCUMENTS

| | | | | |
|---|---|---|---|---|
| 696,120 | A | * | 3/1902 | Vanderpool ............ A61C 19/04 33/513 |
| 709,834 | A | * | 9/1902 | Vanderpool ............ A61C 19/04 33/513 |

(Continued)

FOREIGN PATENT DOCUMENTS

| | | |
|---|---|---|
| JP | 3047733 | 4/1998 |
| KR | 10-2013-0030336 | 3/2013 |

(Continued)

OTHER PUBLICATIONS

English Abstract of 10-2013-0030336.

(Continued)

*Primary Examiner* — Nicholas D Lucchesi
(74) *Attorney, Agent, or Firm* — Studebaker Brackett PLLC (57) ABSTRACT

The present disclosure relates to an auxiliary apparatus used to capture an image of teeth of a patient, and more particularly, to a support block that enables an image of teeth of the patient to be captured in a state where a natural dentition is maintained, and an imaging apparatus including the same. According to the dental support block of the present disclosure and the imaging apparatus including the same, imaging can be performed by reflecting a patient's normal occlusal state, thereby accurately checking and diagnosing a condition of teeth, dentition, and the like and treating accordingly.

7 Claims, 7 Drawing Sheets

(56) References Cited

U.S. PATENT DOCUMENTS

| | | | | |
|---|---|---|---|---|
| 833,204 A * | 10/1906 | Crawford | A61C 19/04 | |
| | | | 433/140 | |
| 1,662,670 A * | 3/1928 | Harter | A61B 5/107 | |
| | | | 33/514 | |
| 1,804,567 A * | 5/1931 | Pray | A61C 19/04 | |
| | | | 33/513 | |
| 2,353,969 A * | 7/1944 | Powers | A61B 6/0407 | |
| | | | 378/177 | |
| 2,552,385 A * | 5/1951 | Scott | A61C 19/04 | |
| | | | 33/514 | |
| 3,521,057 A * | 7/1970 | Morlan | A61B 6/0478 | |
| | | | 378/208 | |
| 3,536,913 A * | 10/1970 | Huchel | A61B 6/14 | |
| | | | 378/168 | |
| 3,936,641 A * | 2/1976 | Heimur | A61B 6/14 | |
| | | | 5/640 | |
| 4,044,265 A * | 8/1977 | Schmidt | A61G 15/00 | |
| | | | 378/208 | |
| 4,782,503 A | 11/1988 | Molitor | | |
| 4,807,272 A * | 2/1989 | Guenther | A61B 6/14 | |
| | | | 378/197 | |
| 9,724,054 B2 * | 8/2017 | Bianconi | A61B 6/04 | |
| 2008/0081312 A1 | 4/2008 | Pruss et al. | | |
| 2008/0253506 A1 * | 10/2008 | Zuendorf | A61B 6/505 | |
| | | | 378/18 | |
| 2012/0321051 A1 * | 12/2012 | Jarva | A61B 6/14 | |
| | | | 378/208 | |
| 2013/0084538 A1 | 4/2013 | Cho | | |
| 2014/0147803 A1 * | 5/2014 | Lecuyer | A61B 6/14 | |
| | | | 433/29 | |
| 2015/0297152 A1 * | 10/2015 | Bianconi | A61B 6/501 | |
| | | | 378/208 | |
| 2020/0078148 A1 * | 3/2020 | Danaei-Moghaddam | A61C 9/0006 | |
| 2022/0071749 A1 * | 3/2022 | Roshkovan | A61C 9/004 | |

FOREIGN PATENT DOCUMENTS

| | | |
|---|---|---|
| KR | 10-2015-0120294 | 10/2015 |
| KR | 10-1560478 | 10/2015 |
| KR | 10-2016-0028551 | 3/2016 |

OTHER PUBLICATIONS

English Abstract of 10-2016-0028551.
English Abstract of 10-1560478.
English Abstract of 10-2015-0120294.
English Abstract of 3047733.

* cited by examiner

DENTAL SUPPORT BLOCK, AND IMAGING DEVICE COMPRISING SAME

TECHNICAL FIELD

The present disclosure relates to an auxiliary apparatus used to capture an image of head and neck, jaw joint, teeth, and the like of a patient, and more particularly, to a support block that enables an image of teeth of the patient to be captured in a state where a natural dentition is maintained, and an imaging apparatus including the same.

BACKGROUND ART

Patients with diseases in the teeth or periodontal diseases are supposed to visit the dentist to treat the diseases, and in dental clinics, X-ray may be performed to check conditions of patients' teeth or alveolar bone in some cases. An X-ray imaging apparatus used in dental clinics causes a certain amount of X-rays to be transmitted through the patient's teeth and detects the intensity of the transmitted X-rays to obtain an image of the patient's teeth or alveolar bone. Recently, computerized tomography (CT), which may capture an image of a slice of a patient's body using X-rays, has commonly been used. The CT includes a three-dimensional (3D) imaging apparatus which projects X-rays to a human body, while rotating at a certain angle through 360 degrees, collects transmitted X-rays through a detector such as a sensor or the like, reconfigures an absorption value for cross-sections of the human body, and displays a corresponding image, a panoramic imaging apparatus which images the whole in a circumferential direction based on an X-ray generator as a two-dimensional (2D) plane so that the entire teeth condition and even a jaw joint can be seen at a glance, and the like.

Figure 1:
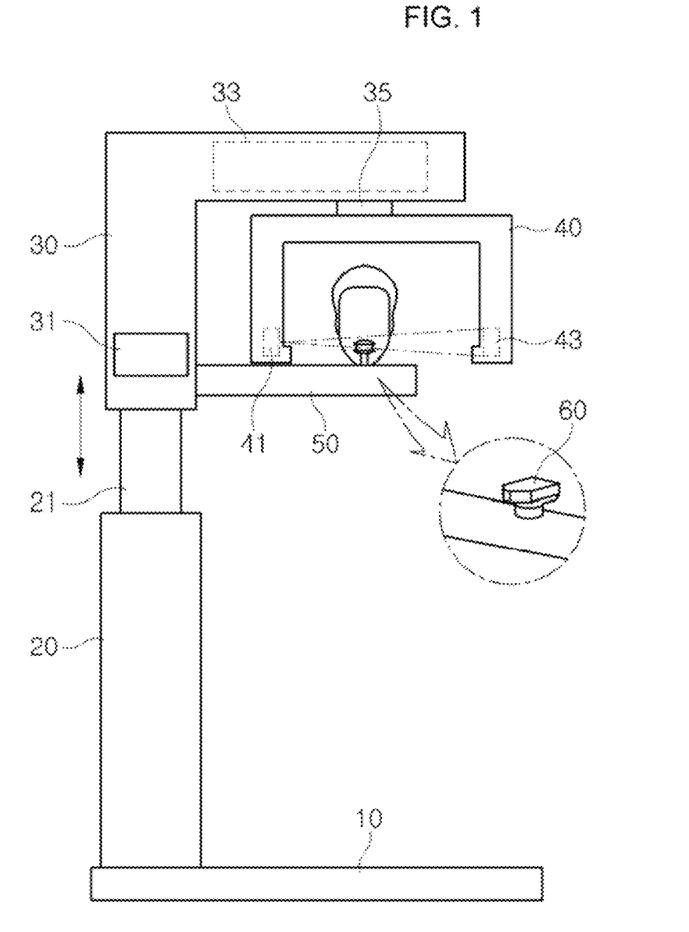
FIG. 1 is a schematic diagram showing the related art dental imaging apparatus.

FIG. 1 is a schematic diagram showing a related art dental imaging apparatus. Referring to FIG. 1, the related art image capturing apparatus may include a base 10, a lower pillar 20, an upper pillar 30, a rotating arm 40, and a support frame 50. The base 10 is a portion supported by a floor surface of a building, and the lower pillar 20 is provided on an upper portion of one side of the base 10 and supported by the base 10 and includes a sliding part 21 extending to be movable in an upward direction. The upper pillar 30 is a portion moving upward and downward along the sliding part 21 of the lower pillar 20, in which a vertical portion and a horizontal portion are integrally formed. An operation panel 31 may be provided on a front portion of the upper pillar 30, and a manager may control the dental imaging apparatus through the operation panel 31. The rotating arm 40 is located below the horizontal portion of the upper pillar 30 and coupled thereto through the rotating shaft 35 to perform a linear motion and a rotary motion. An X-ray light source 41 and an X-ray sensor 43 are provided on opposing sides of the rotating arm 40, respectively. X-rays irradiated from the X-ray light source 41 transmits through the patient's face, is subsequently detected by the X-ray sensor 43, and is converted into an electrical signal. The electrically converted signal is processed into image data readable by a controller 33 provided in the rotating arm 40. The support frame 50 protrudes in a horizontal direction from the vertical portion of the upper pillar 30 to support a face part of the patient whose images of teeth, dentition, or alveolar bone are to be captured. Here, an occlusal bite block 60 that the patient bites between teeth so as to be fixed is provided on an upper portion of the support frame 50 for accurate imaging of teeth or dentition.

Figure 2A:
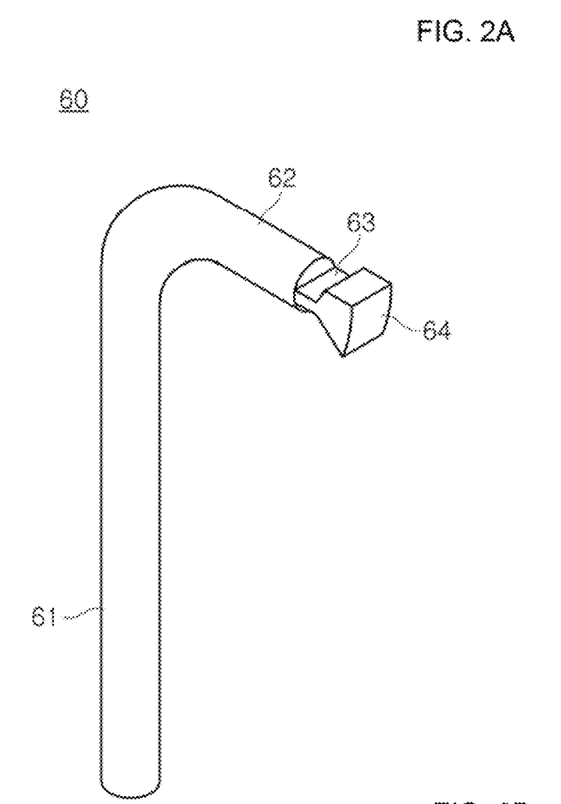
FIG. 2A is a perspective view of the related art bite block.
Figure 2B:
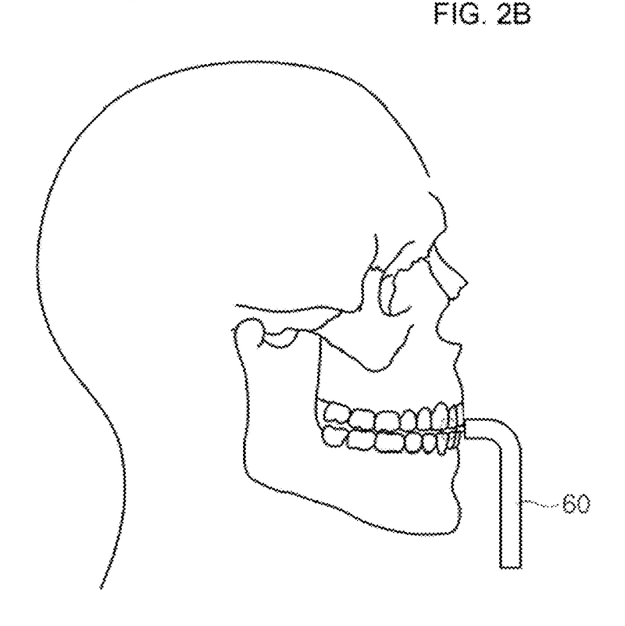
FIG. 2B is a view showing a screen example when a patient bites the related art bite block.
Figure 2C:
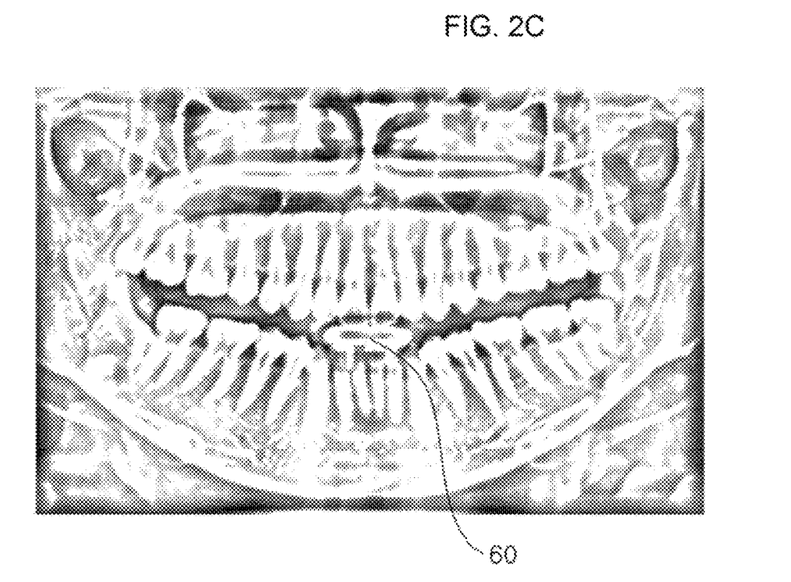
FIG. 2C is an exemplary view showing an image of patient's teeth using the related art bite block.

FIG. 2A is a perspective view of the related art bite block and FIG. 2B is a view showing a screen example of a patient who bites the related art bite block. FIG. 2C is an exemplary view of an image of patient's teeth captured using the related art bite block. First, referring to FIG. 2A, the related art bite block 60 includes a rod-shaped handle portion 61 having a predetermined length, a horizontal portion 62 bent at a right angle from the handle portion 61 in a state where the handle portion 61 is vertically erected, a teeth recess 63 provided at an end of the horizontal portion 62 and allowing a patient to bite the bite block 60 with upper and lower teeth. In addition, a protrusion 64 protruding to be caught in the patient's mouth is provided at a front portion of the teeth recess 63.

Imaging is performed on parts such as teeth or dentition of the patient with the patient biting the bite block 60 as shown in FIG. 2B. Here, however, since the patient strongly fixes the bite block 60 with the upper or lower teeth, it is difficult to reflect a natural occlusal state. When the user bites the bite block 60 with the front teeth, a space inherent to the bite block 60 exists in the user's mouth and a jaw joint is also moved to an abnormal position, and in this state, imaging is performed. As a result, the occlusal state of the user is different from a normal state, thus making it difficult to accurately capture an image reflecting the patient's normal occlusal state.

In order to solve the problem, Korean Patent Laid-open Publication No. 10-2013-0030336 (entitled Panoramic Image Acquiring Apparatus) discloses that a location sensor is mounted at a position on one side of a bite block to recognize an alignment position of teeth, Korean Patent Laid-open Publication No. 10-2016-0028551 (entitled Dental Bite Block) discloses that images of a patient and a bite block are extracted together by improving a material of a bite block, and Korean Patent Registration No. 10-1560478 (entitled Guide for Aligning Examinee) discloses that an annular alignment member is provided on an extending line of a bite block.

However, alignment states of some patients may be improved by the related art but the problem of not reflecting a normal occlusal state because a patient strongly fixes the bite block between the teeth is not fundamentally resolved.

RELATED ART DOCUMENT

Korean Patent Laid-open Publication No. 10-2013-0030336 (2013 Mar. 27)

Korean Patent Laid-open Publication No. 10-2016-0028551 (2016 Mar. 14)

Korean Patent Registration No. 10-1560478 (2015 Oct. 14)

DISCLOSURE

Technical Problem

An aspect of the present disclosure provides a dental support block capable of supporting a philtrum and lower jaw part of a patient, rather than teeth of the patient, thus enabling imaging with a normal occlusal state maintained.

Technical Solution

According to an aspect of the present disclosure, there is provided a dental support block for a dental imaging apparatus including: a mental protuberance support portion configured to support a jaw part of a user; a pedestal provided under the mental protuberance support portion to support the user's face; a sliding operation portion configured such that a portion thereof is inserted into the mental protuberance support portion through a groove provided at an upper portion of the mental protuberance support portion; and an upper surface mounting portion bent from an upper end of the sliding operation portion and brought into contact with a part under a nose or a philtrum part of the user.

The sliding operation portion may have a scale provided on a surface thereof so that a position of the upper surface mounting portion is checked according to users.

The sliding operation portion and the upper surface mounting portion may be formed of at least one material of plastic, carbon fiber, and a synthetic resin.

The dental support block may further include a face support frame configured to fix the user's face to the dental imaging apparatus.

The face support frame may include a front frame supporting a front part of the user's face and a rear frame supporting a rear part of the user's face.

According to another aspect of the present disclosure, there is provided a dental support block for a dental imaging apparatus including: a mental protuberance support portion configured to support a jaw part of a user; a pedestal provided under the mental protuberance support portion to support the user's face; a main body coupling portion configured to allow the mental protuberance support portion and the pedestal to be coupled to a side surface thereof; a sliding operation portion configured such that a portion thereof is inserted into the mental protuberance support portion through a groove provided at an upper portion of the main body coupling portion; and an upper surface mounting portion bent from an upper end of the sliding operation portion and brought into contact with a part under a nose or a philtrum part of the user.

According to another aspect of the present disclosure, there is provided a dental imaging apparatus including: a base supported by a floor surface of a building; a lower pillar provided at an upper portion of one side of the base and configured to support the base in an upward direction; a sliding member extending from the lower pillar so as to be movable in the upward direction; an upper pillar configured to be movable up and down along the sliding member; a rotating arm coupled to one side of the upper pillar and configured to irradiate X-rays to a facial part of the user at a designated position through a linear or rotary motion; and a face support frame provided on one side of the upper pillar and configured to support the user's face, wherein the face support frame includes: a mental protuberance support portion configured to support a jaw part of a user; a pedestal provided under the mental protuberance support portion to support the user's face; a sliding operation portion configured such that a portion thereof is inserted into the mental protuberance support portion through a groove provided at an upper portion of the mental protuberance support portion; and an upper surface mounting portion bent from an upper end of the sliding operation portion and brought into contact with a part under a nose or a philtrum part of the user.

The face support frame may further include a front frame supporting a front portion of the user's face and a rear frame supporting a rear portion of the user's face.

Advantageous Effects

According to the dental support block of the present disclosure and the imaging apparatus including the same, imaging can be performed by reflecting a patient's normal occlusal state, thereby accurately checking and diagnosing a condition of a head and neck, a jaw joint, teeth or dentition, and the like and treating accordingly.

BEST MODES

The terminologies used herein are only for describing particular embodiments and are not intended to limit the present disclosure. Singular forms as used herein include plural forms unless stated otherwise. The term "comprise" as used herein is used to embody a particular characteristic, region, integer, step, operation, element, and/or component without excluding presence or addition of other particular characteristics, regions, integers, steps, elements, components, and/or groups.

The terms "upper," "top," "lower," "bottom," left," and "right" as used herein refer to relative relations in positions among the elements shown in the drawings and should not be intended to limit the present disclosure. The terms "first," "second," "third," and "fourth" as used herein are used in the following detailed description to refer to various elements, regions, or sections, but such elements, regions, or sections should not be limited by the terms. The terms are used merely to distinguish one element, region, or section from another. Therefore, the term "first element," "first region, or first section" as used herein should also be termed a "second element," "second region," or "second section" without departing form the scope of the present disclosure.

Unless defined otherwise, all terms including the technical or scientific terms as used herein have the same meaning as those commonly appreciated by one of ordinary skill in the art to which the present disclosure pertains. The terms defined in dictionaries commonly used may be construed to comply with those set forth herein and relevant technical documents and should not be interpreted overly ideally or formally unless defined otherwise.

Hereinafter, preferred embodiments of the present disclosure are described in detail with reference to the accompanying drawings.

Figure 3A:
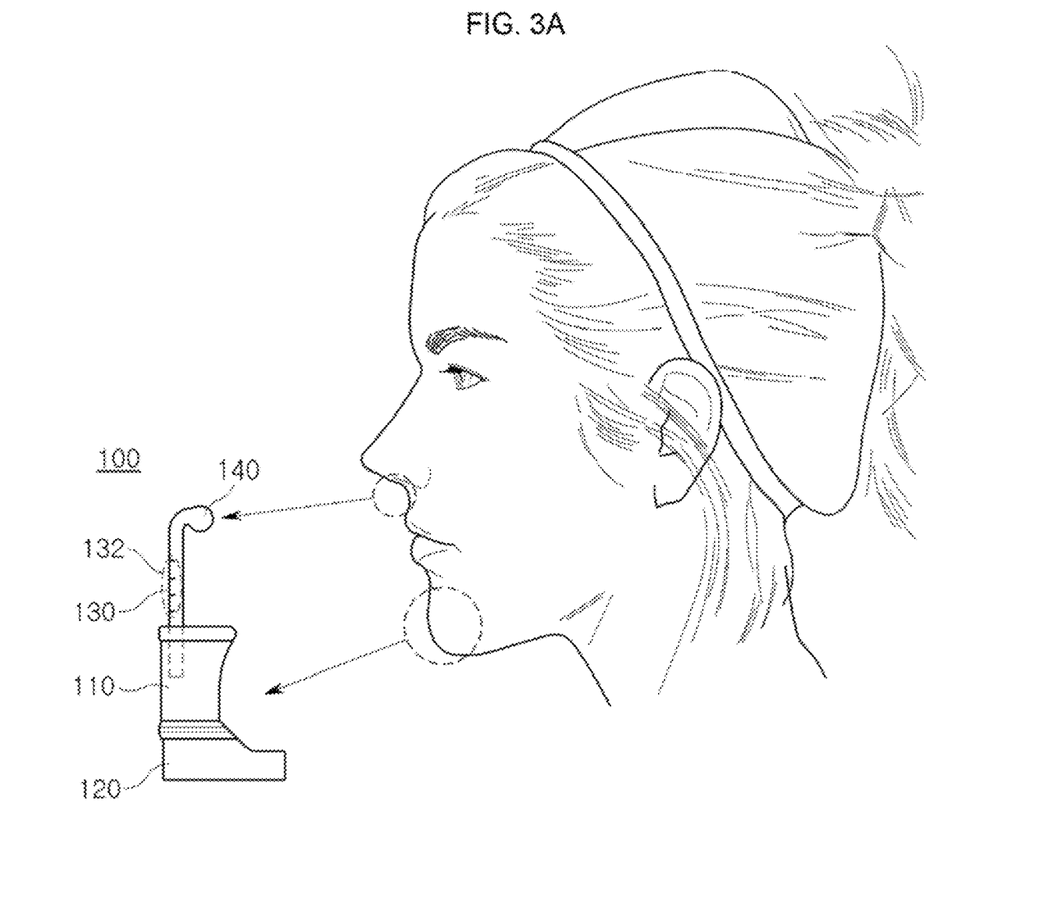
FIG. 3A is a perspective view of a dental support block according to an embodiment of the present disclosure.
Figure 3B:
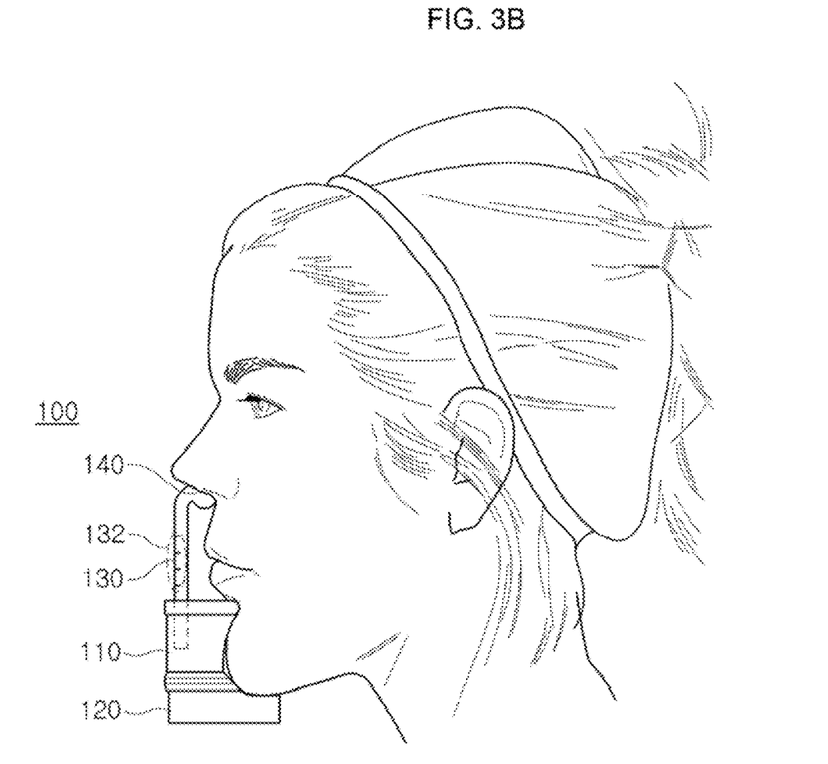
FIG. 3B is an exemplary view showing a screen in the case of supporting a user's face on a dental support block according to an embodiment of the present disclosure.
Figure 3C:
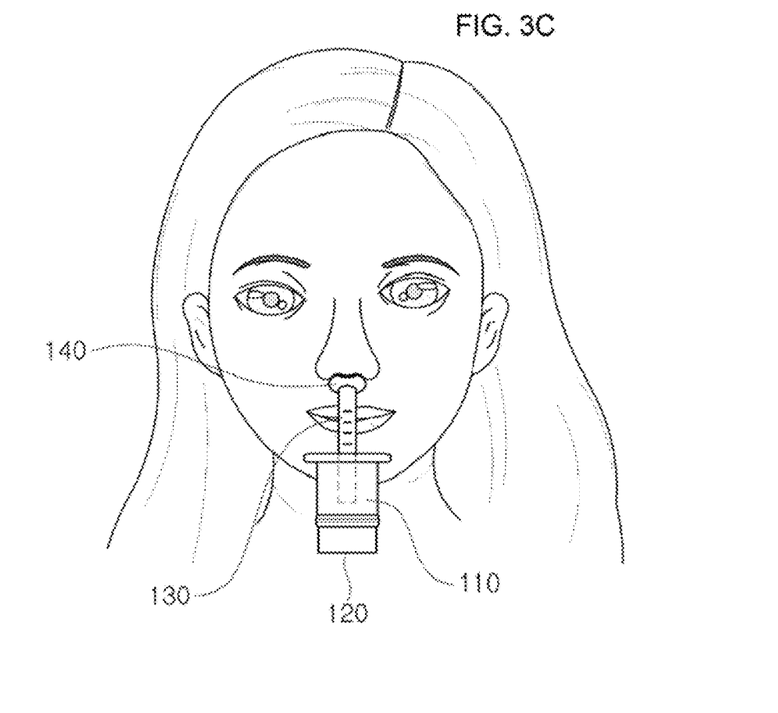
FIG. 3C is an exemplary view showing a screen in the case of supporting a user's face on a dental support block 100 of the present disclosure.

FIG. 3A is a perspective view of a dental support block according to an embodiment of the present disclosure, FIG. 3B is an exemplary view showing a screen in the case of supporting a user's face on a dental support block according to an embodiment of the present disclosure, and FIG. 3C is an exemplary view showing a screen in the case of supporting a user's face on a dental support block 100 of the present disclosure. First, referring to FIGS. 3A and 3B, the dental support block 100 of the present disclosure includes a jaw protuberance support portion 110, a pedestal 120, a sliding operation portion 130, and an upper surface mounting portion 140.

The mental protuberance support portion 110 is a portion which comes into contact with a mental protuberance part of a user when the user moves his or her face forward to capture an image of teeth or dentition. Therefore, the mental protuberance support portion 110 may serve to guide movement forward and positioning when the user captures an image of the teeth or dentition.

The pedestal 120 is a portion located at the bottom of the mental protuberance support portion 110 and attached to a dental imaging apparatus to support the user's face. Here, a portion of the pedestal 120 may be in contact with and support a lower portion of the user's mental protuberance and serve to stably support the user's face when the image of the teeth or dentition of the user is captured.

The sliding operation portion 130 has of a cylindrical rod structure having a diameter smaller than the mental protuberance support portion 110, and a partial lower portion thereof may enter or leave from the inside of the mental protuberance support portion 110 in a sliding manner through a groove provided in the mental protuberance support portion 110. This is to adjust a shape of the dental support block 100 to fit the user's facial structure because each user has different facial structures or shapes and different distances between noses and mental protuberances. In addition, the sliding operation portion 130 may have a scale 132 on a surface thereof to check a position of the sliding operation portion 130 after the support block 100 is adjusted according to the user's facial structure and used. Therefore, after capturing an image of the teeth or dentition by adjusting the sliding operation portion 130 according to his or her facial structure, the user may check a positional relation between the sliding operation portion 130 and the mental protuberance support portion 110 by the scale 132. Thereafter, when an imaging is performed again afterward, the user may easily adjust the position of the sliding operation portion 130 according to his or her facial structure.

The upper surface mounting portion 140 is a portion bent in an "L" shape from an upper end of the sliding operation portion 130, which comes into contact with a part under a nose and a philtrum part of the user. The upper surface mounting portion 140 may be long or short in length depending on the user's facial structure and may be configured to be slidable.

After brining the mental protuberance support portion 110 into tight contact with his or her mental protuberance part, the user may bring the upper surface mounting portion 140 into contact with the part under the nose and the philtrum part by adjusting the sliding operation portion 130 in an up-down direction to adjust a shape of the support block 100 according to his or her facial structure.

The dental support block 100 of the present disclosure may be formed of transparent or colored plastic, carbon fiber, or synthetic resin. The synthetic resin may include a nylon resin, polycarbonate resin, a polyethylene resin, an acrylonitrile-butadiene-styrene (ABS) resin, or the like. Also, the dental support block 100 may be formed of a mixture of a carbon fiber and a synthetic resin.

When the user captures an image using the dental support block 100 of the present disclosure, the user may bring an end portion of the upper surface mounting portion 140 into close contact with the philtrum part under the nose and bring a front part of the mental protuberance into contact with the mental protuberance support portion 110 as shown in FIG. 3C, and in this state, a base part of the lower jaw may be stably supported by the pedestal 120. In this case, the upper jaw (maxilla) and the lower jaw (mandible) of the user may be in a natural occlusal state, and thus imaging may be performed in the accurate occlusal state.

Figure 4:
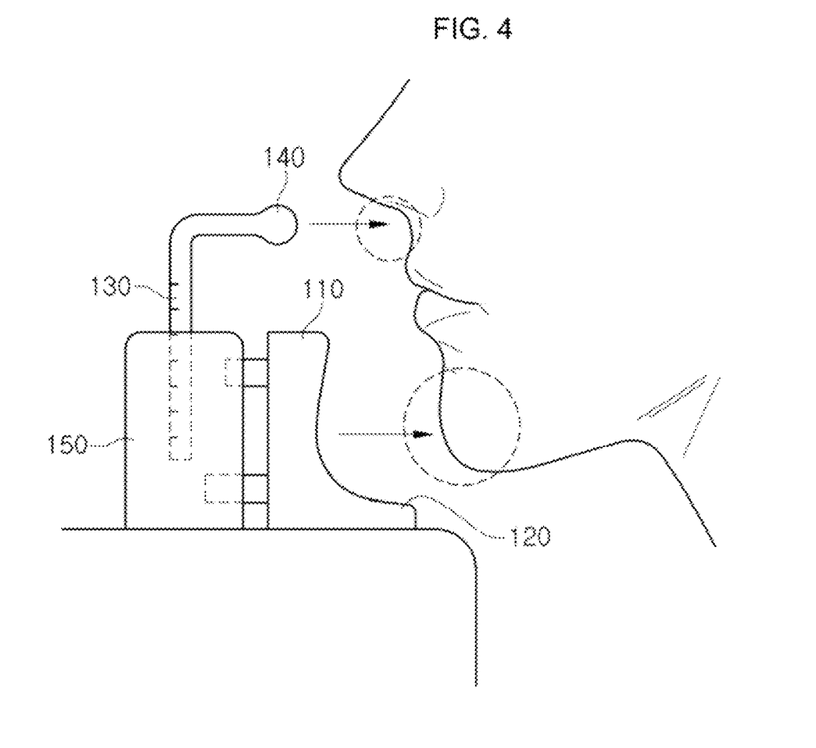
FIG. 4 is a perspective view of a dental support block according to another embodiment of the present disclosure.

FIG. 4 is a perspective view of a dental support block according to another embodiment of the present disclosure. Referring to FIG. 4, the dental support block 100 of the present disclosure may include a mental protuberance support portion 110, a pedestal 120, a sliding operation portion 130, and an upper surface mounting portion 140. These elements may be integrally configured or may be separately configured and coupled through a main body coupling portion 150. That is, in a state where the main body coupling portion 150 is fixed to the dental imaging apparatus, the mental protuberance support portion 110 supporting the user's jaw part and the pedestal 140 are coupled as one component to one side of the main body coupling portion 150 and the upper surface mounting portion 140 supporting a part under the nose or a philtrum part of the user and the sliding operation portion 130 may be coupled as one component to an upper portion of the main body coupling portion 150. Of course, the mental protuberance support portion 110 and the pedestal 120 may be separately coupled to the main body coupling portion 150.

As such, in case where the mental protuberance support portion 110, the pedestal 120, the sliding operation portion 130, and the upper surface mounting portion 140 are configured as individual components or configured to be coupled through one or more components, the dental support block 100 may be configured in various combinations by changing a size or shape of required components according to the user's facial shape.

Figure 5:
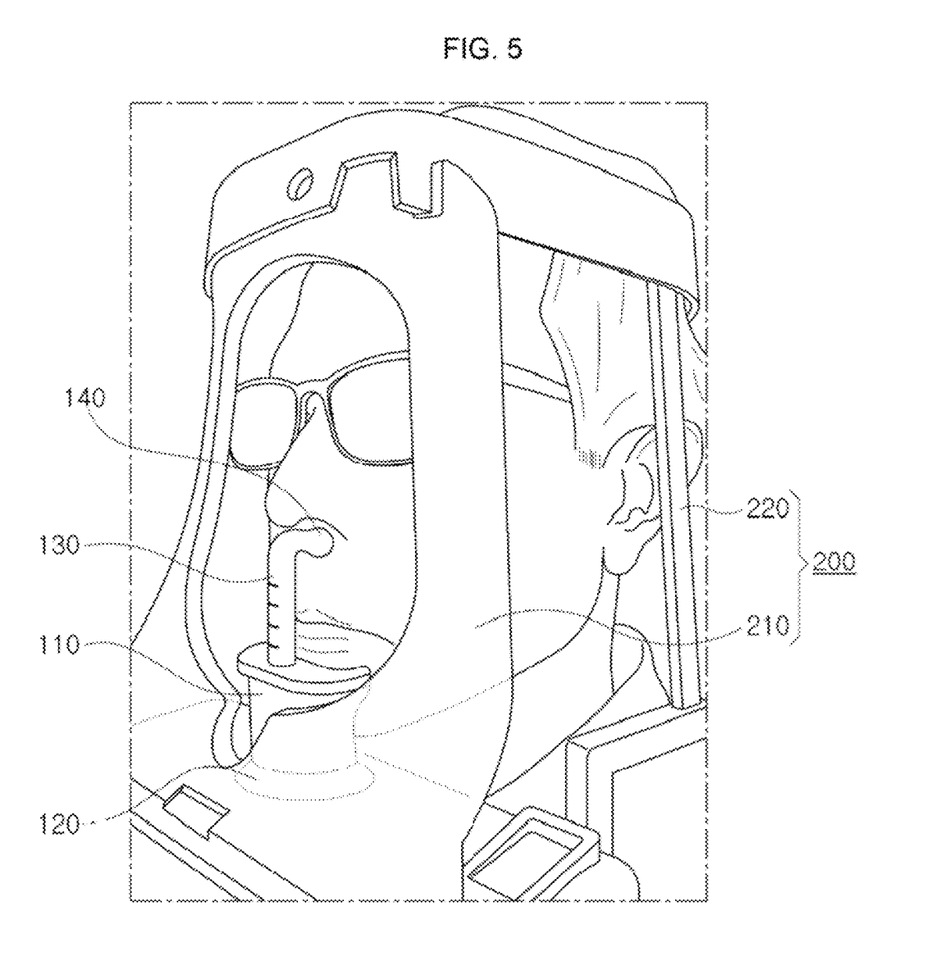
FIG. 5 is an exemplary view showing a screen when a user captures an image using a dental support block according to an embodiment of the present disclosure.

FIG. 5 is an exemplary view showing a screen when a user captures an image using the dental support block 100 according to an embodiment of the present disclosure. Referring to FIG. 5, the dental support block 100 of the present disclosure is located at a face mounting portion such that an oral part of the user faces an X-ray light source of the imaging apparatus to capture an image of the head and neck, jaw joint, teeth or dentition, and the like through the dental imaging apparatus.

Here, the support block 100 of the present disclosure is configured to support the user's nose and the mental protuberance part of the user. However, since the user may move the face in the directions of up, down, left, and right, and thus, the support block 100 may include a face support frame 200 serving to fix the user's face.

The face support frame 200 may include a front frame 210 for supporting a front part of the user's face and a rear frame 220 for supporting a rear part of the user's face. The front frame 210 and the rear frame 220 may be integrally or separately formed.

The front frame 210 is open in a middle portion of a front surface thereof with respect to the front of the user for image capturing but has a circular structure along a circumference of the face so that the user may bring his or her face into close contact therewith in a forward direction. Here, when the user brings the face into close contact with the front frame 210 in the forward direction, the rear frame 220 may be brought into close contact with the back of the user's face and fixed to the user's face using a belt or the like so that the user's face may not move backward.

A process in which the user captures an image of the head and neck, jaw joint, teeth or dentition, and the like using the support block 100 of the present disclosure may be performed as follows.

First, the user may place the upper surface mounting portion 140 at a part under the nose and the philtrum part of the user by adjusting the sliding operation portion 130 of the support block 100 and brings the mental protuberance support portion 110 into close contact with the user's mental protuberance part so as to be in contact with the user's mouth part. Here, the support block 100 may be located such that the user's mouth part faces the X-ray light source of the dental imaging apparatus. Since the support block 100 of the present disclosure is not a structure bitten in an oral cavity of the user using teeth, the user may maintain a natural oral structure as usual. Therefore, the oral structure of the user as usual may be reflected as it is in treating teeth or manufacturing correcting or assisting devices.

Thereafter, the front frame 210 and the rear frame 220 may be attached and fixed to the user's face so that the user is located in a fixed form for capturing an image of the head and neck, jaw joint, teeth or dentition, and the like. In this state, an oral structure such as a user's teeth or dentition is captured by X-rays using the dental imaging apparatus.

Figure 6:
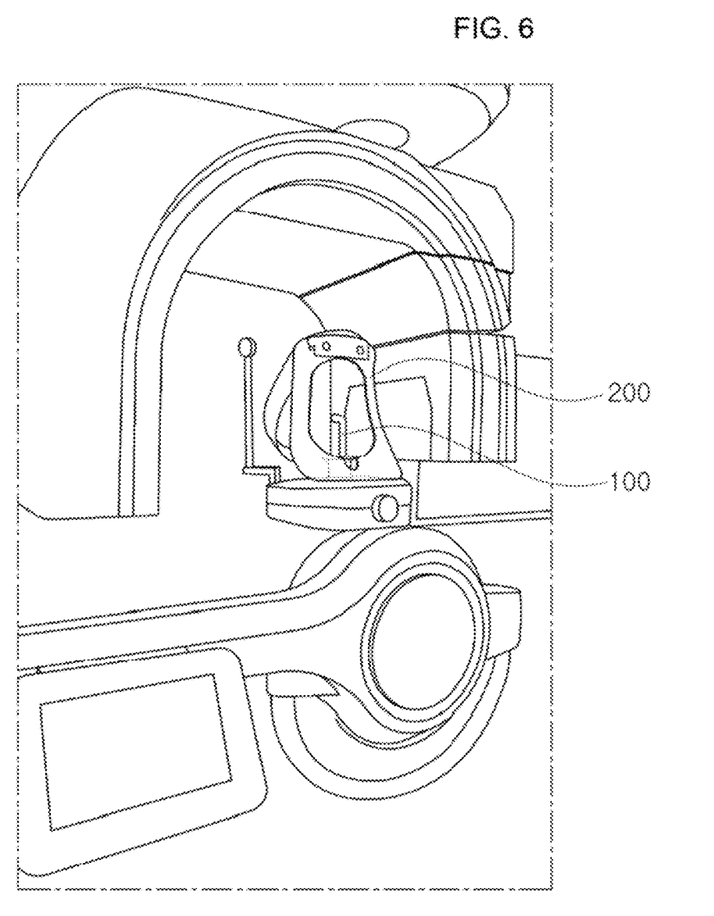
FIG. 6 is an exemplary view of a screen when a dental support block according to an embodiment of the present disclosure is mounted on a dental imaging apparatus.

FIG. 6 is an exemplary view of a screen when a dental support block according to an embodiment of the present disclosure is mounted on a dental imaging apparatus. Referring to FIG. 6, the dental support block 100 of the present disclosure may be used in a 3D CT apparatus such as a cone beam CT. In addition, the support block 100 of the present disclosure may be configured as an integral component provided together with the dental imaging apparatus or may be configured as an independent component which can be separately attached to various dental imaging apparatuses. In addition, as shown in FIG. 4, when the dental support block 100 is configured in an assemblable form, the dental support block 100 may be configured to include the main body coupling portion 150 attached to the dental imaging apparatus and a plurality of components which can be coupled to the main body coupling portion 150.

As described above, in case where an image of the head and neck, jaw joint, teeth or dentition, and the like of the user is captured using the dental support block of the present disclosure, the teeth or dentition of the user can be treated or an auxiliary device may be manufactured by reflecting the natural oral structure of the user as usual as it is.

Although the embodiments of the present disclosure have been described above with reference to the accompanying drawings, a person skilled in the art to which the present disclosure pertains will understand that the present disclosure may be implemented in any other specific forms without changing the technical spirit or essential features thereof. Therefore, it should be understood that the embodiments described above are exemplary in all respects and not restrictive. The scope of the present disclosure is defined by the appended claims, rather than the detailed description, and should be construed as including all modifications and variations derived from the meaning and scope of the claims and concept equivalent thereto.

| 100: dental support block | 110: mental protuberance support portion |
|---|---|
| 120: pedestal | 130: sliding operation portion |
| 132: scale | 140: upper surface mounting portion |
| 150: main body coupling portion | 200: face support frame |
| 210: front frame | 220: rear frame |

The invention claimed is:

1. A dental support block for a dental imaging apparatus, the dental support block comprising:
   a first part comprising:
      a mental protuberance support portion configured to support a jaw part of a user;
      a pedestal provided under the mental protuberance support portion, and configured to support a face of the user;
   a main body coupling portion; and
   a second part comprising:
      a sliding operation portion having a lower end portion configured to be inserted into a groove of the main body coupling portion, the groove is provided at a top surface of the main body coupling portion; and
      an upper surface mounting portion bent from an upper end of the sliding operation portion and is slidable wherein a distal end of the upper surface mounting portion contacts with a part under a nose and an upper part of a philtrum of the user,
   wherein the first part is coupled to a sidewall of the main body coupling portion, via connecting bars, and
   wherein the second part is coupled with the main body coupling portion, via the lower end portion of the sliding operation portion and the groove provided at the top surface of the main body coupling portion.

2. The dental support block of claim 1, wherein a height of the first part and a height of the main body coupling portion are the same.

3. The dental support block of claim 1, wherein in the first part, a first side of the mental protuberance support portion and a first side of the pedestal configure a straight side wall of the first part, and a second side of the mental protuberance support portion and a second side of the pedestal configure a continuously curved side wall of the first part.

4. The dental support block of claim 3, wherein the straight side wall of the first part is facing with the sidewall of the main body coupling portion, with having a distance between the straight side wall of the first part and the sidewall of the main body coupling portion.

5. The dental support block of claim 1, wherein the sliding operation portion and the upper surface mounting portion are formed of at least one material of plastic, carbon fiber, and a synthetic resin.

6. The dental support block of claim 1, further comprising a face support frame configured to fix the user's face to the dental imaging apparatus.

7. The dental support block of claim 6, wherein the face support frame comprises:
   a front frame adapted to support a front part of the user's face; and
   a rear frame adapted to support a rear part of the user's face.

* * * * *